(12) United States Patent
Bedoukian

(10) Patent No.: US 10,703,705 B2
(45) Date of Patent: *Jul. 7, 2020

(54) CONTROL AND REPELLENCY OF BED BUGS

(71) Applicant: BEDOUKIAN RESEARCH, INC., Danbury, CT (US)

(72) Inventor: Robert H. Bedoukian, West Redding, CT (US)

(73) Assignee: Bedoukian Research, Inc., Danbury, CT (US)

( * ) Notice: Subject to any disclaimer, the term of this patent is extended or adjusted under 35 U.S.C. 154(b) by 171 days.

This patent is subject to a terminal disclaimer.

(21) Appl. No.: 14/390,081

(22) PCT Filed: Apr. 30, 2013

(86) PCT No.: PCT/US2013/000122
§ 371 (c)(1),
(2) Date: Oct. 2, 2014

(87) PCT Pub. No.: WO2013/165478
PCT Pub. Date: Nov. 7, 2013

(65) Prior Publication Data
US 2015/0152038 A1    Jun. 4, 2015

Related U.S. Application Data

(60) Provisional application No. 61/687,918, filed on May 2, 2012.

(51) Int. Cl.
*A01N 43/16*    (2006.01)
*A01N 43/08*    (2006.01)
(Continued)

(52) U.S. Cl.
CPC ............ *C07C 69/675* (2013.01); *A01N 31/06* (2013.01); *A01N 35/06* (2013.01); *A01N 37/02* (2013.01);
(Continued)

(58) Field of Classification Search
CPC ........ A01N 31/06; A01N 43/16; A01N 43/08; C07D 309/30; C07D 307/58
See application file for complete search history.

(56) References Cited

U.S. PATENT DOCUMENTS 3,700,694 A * 10/1972 Siddall ................. C07D 307/58
549/295
5,017,377 A * 5/1991 Sikinami ................. A01N 25/18
514/729
(Continued)

FOREIGN PATENT DOCUMENTS

JP    2007-504227 A    3/2007
JP    2010-530036 A    9/2010
(Continued)

OTHER PUBLICATIONS

CAS Registry No. 24851-98-7 (Nov. 16, 1984).*
(Continued)

*Primary Examiner* — Bethany P Barham
*Assistant Examiner* — Peter Anthopolos
(74) *Attorney, Agent, or Firm* — Ohlandt, Greeley, Ruggiero & Perle, LLP

(57) ABSTRACT

Control or repellency of bed bugs is accomplished by bringing the bed bugs into contact with at least one of the compounds of the structure (I); wherein R is selected from —OH, —OC(O)$R_4$, —O$R_6$, —(O$R_6$)$_2$, wherein each $R_6$ is independently selected from an alkyl group containing from 1 to 4 carbon atoms and $R_4$ is a branched or straight chain saturated or unsaturated hydrocarbyl group with zero to two double bonds and from 1 to 15 carbon atoms; X is O or $CH_2$, with the proviso that when X is O R can only be =O; each Z is independently selected from (CH) and ($CH_2$) y is a numeral selected from 1 and 2; $R_1$ is selected from H or a branched or straight chain saturated or unsaturated hydrocarbyl group with zero to two double bonds and from 1 to 15 carbon atoms. $R_2$ is selected from H and a branched or straight chain saturated or unsaturated hydrocarbyl group with zero to three double bonds and from 1 to 15 carbon atoms. $R_3$ is selected from H, a branched or straight chain, saturated or unsaturated hydrocarbyl group with zero to three double bonds and from 1 to 15 carbon atoms, —($CH_2$)$_n$OH, —C(O)O$R_5$, —$CH_2$C(O)O$R_7$, —$CH_2$C(O)$R_8$, —C(O)N$R_9$$R_{10}$, —$CH_2$C(O)N$R_{11}$$R_{12}$ where each of $R_5$, $R_7$, $R_8$, $R_9$, $R_{10}$, $R_{11}$ and $R_{12}$ is independently selected from H and a branched or straight chain, saturated or unsaturated hydrocarbyl group with zero to three double bonds and from 1 to 15 carbon atoms, and n is an integer of from 1 to 12; and the bond between the 2 and 3 positions in the ring structure may be a single or a double bond, and wherein the compounds of structure (1) contain from 11 to 20 total carbon atoms, except where R is =O, X=$CH_2$ and y is 1 the compounds of structure (I) contain from 13 to 20 total carbon atoms in the compounds, wherein the compounds of structure (1) contain from 11 to 20 total carbon atoms, except where R is =O, X=CH2 and y is 1 the compounds of structure (I) contain from 13 to 20 total carbon atoms in the compounds, wherein the compounds of structure (1) contain from 11 to 20 total carbon atoms, except where R is =0, X=$CH_2$ and y is 1 the compounds of structure (I) contain from 13 to 20 total carbon atoms in the compounds.

(I)

12 Claims, No Drawings

(51) Int. Cl.

| | | |
|---|---|---|
| *A01N 31/06* | (2006.01) | |
| *C07D 309/30* | (2006.01) | |
| *C07D 307/58* | (2006.01) | |
| *C07C 69/675* | (2006.01) | |
| *A01N 37/18* | (2006.01) | |
| *A01N 49/00* | (2006.01) | |
| *A01N 35/06* | (2006.01) | |
| *A01N 37/02* | (2006.01) | |
| *A01N 37/22* | (2006.01) | |
| *A01N 37/36* | (2006.01) | |
| *A01N 37/42* | (2006.01) | |
| *C07C 35/06* | (2006.01) | |
| *C07C 35/18* | (2006.01) | |
| *C07C 59/205* | (2006.01) | |
| *C07C 69/708* | (2006.01) | |
| *C07C 235/74* | (2006.01) | |
| *C07D 307/33* | (2006.01) | |

(52) U.S. Cl.
CPC .............. *A01N 37/18* (2013.01); *A01N 37/22* (2013.01); *A01N 37/36* (2013.01); *A01N 37/42* (2013.01); *A01N 43/08* (2013.01); *A01N 43/16* (2013.01); *A01N 49/00* (2013.01); *C07C 35/06* (2013.01); *C07C 35/18* (2013.01); *C07C 59/205* (2013.01); *C07C 69/708* (2013.01); *C07C 235/74* (2013.01); *C07D 307/33* (2013.01); *C07D 309/30* (2013.01); *C07C 2601/08* (2017.05); *C07C 2601/16* (2017.05)

(56) References Cited

U.S. PATENT DOCUMENTS

| | | | |
|---|---|---|---|
| 5,298,250 A | * | 3/1994 | Lett .................... A01N 49/00 424/405 |
| 7,579,016 B2 | | 8/2009 | Zhang et al. |
| 8,142,801 B2 | | 3/2012 | Jones |
| 8,481,594 B2 | | 7/2013 | Boulle et al. |
| 8,551,510 B2 | | 10/2013 | Bedoukian |
| 8,728,506 B2 | | 5/2014 | Ono |
| 2008/0020087 A1 | | 1/2008 | Landers |
| 2009/0018192 A1 | | 1/2009 | Zhang et al. |
| 2010/0069497 A1 | | 3/2010 | Boulle et al. |
| 2010/0227010 A1 | | 9/2010 | Jones |
| 2012/0030882 A1 | | 2/2012 | Wetrosky et al. |
| 2012/0046359 A1 | | 2/2012 | Bedoukian |
| 2012/0171313 A1 | | 7/2012 | Boone |
| 2012/0213836 A1 | | 8/2012 | Ono |

FOREIGN PATENT DOCUMENTS

| | | | | |
|---|---|---|---|---|
| JP | 2015-521171 A | | 7/2015 | |
| WO | 2010126576 A1 | | 11/2010 | |
| WO | WO 2010126576 A1 | * | 11/2010 | ............ A01N 35/02 |
| WO | 2011040252 A1 | | 4/2011 | |
| WO | 2013/050967 A1 | | 4/2013 | |
| WO | 2013050967 A1 | | 4/2013 | |
| WO | 2013165475 A1 | | 11/2013 | |
| WO | 2013165478 A1 | | 11/2013 | |
| WO | 2014028835 A2 | | 2/2014 | |
| WO | 2014031790 A1 | | 2/2014 | |
| WO | 2014099821 A2 | | 6/2014 | |

OTHER PUBLICATIONS

CAS Registry No. 68133-79-9 (Nov. 16, 1984).*
European Office Action dated Dec. 21, 2015 from corresponding European Patent Application No. 13784107.8, 16 pages.
Japanese Office Action dated Feb. 2, 2016 from corresponding Japanese Application No. JP 2015-510250, 10 pages.
Japanese Office Action dated May 24, 2016 from corresponding Japanese Application No. JP 2015-510250, 4 pages.
International Search Report dated Jul. 15, 2013 from PCT/US2013/000122, 4 pages.
Written Opinion dated Jul. 15, 2013 from PCT/US2013/000122, 12 pages.
Wang, et al., "Repellants for Bed Bugs", Journal of Economic Entomology, Dec. 2013, 8 pp.
Supplementary European Search Report dated Sep. 28, 2015 from corresponding European Application No. 13784107.8, 7 pages.
First Office Action dated Oct. 9, 2015 from corresponding Chinese Application No. 201380022819.1, 10 pages.
EP Office Action for Application No. EP 13784107.8, dated Jun. 1, 2017, 7 pages.
European Office Action dated Nov. 9, 2016 from corresponding European Application No. 13 784 107.8, 11 pages.
Extended European Search Report for the corresponding application EPV 17180969.2, dated Sep. 25, 2017, 11 pages.
European Communication for the corresponding European divisional application 17180969.2, dated Aug. 2, 2018, 6 pages.
European Communication for the corresponding European application 17180969.2, dated Jul. 9, 2019, 6 pages.
European Communication for the corresponding European application 13784107.8, dated Jun. 12, 2019, 6 pages.
Wang, et al., "Repellency of Selected Chemicals Against the Bed Bug (Hemiptera: Cimicidae)", Journal of Economic Entomology, vol. 106, Issue 6 Dec. 2013, pp. 2522-2529.
European Office Action dated Dec. 18, 2019 from corresponding European Patent Application No. 17 180 969.2, 5 pages.

* cited by examiner

CONTROL AND REPELLENCY OF BED BUGS

FIELD OF THE INVENTION

This invention relates to compounds used as agents to control and repel bed bugs.

BACKGROUND TO THE INVENTION

Recent data suggests bed bug infestations (*Cimex* species) of human domiciles are on the rise. At least 92 species of bed bugs have been identified globally, of which at least 16 species are in the North American continent. Generally, bed bugs are parasitic pests with its hosts including humans and various domesticated animals. It is believed that bed bug infestations are becoming more problematic now at least in part because long acting, residual insecticides are no longer being used to keep bed bug populations in check. In addition, increased international travel and insecticide resistance have made bed bug infestations spread and made control with insecticides very difficult. In terms of scale, such infestations are of particular concern for hoteliers, cruise ships, trains, daycare facilities, and the like because of the business reputation risk posed by bad press or bad reviews. Other problematic areas tend to include nursing homes, barracks, dorms, hospitals, and various other forms of high density housing. Nonetheless, single family homes can likewise be impacted adversely.

Bed bugs feed on human blood. Thus, bed bugs are not merely unsightly, they leave ugly skin markings. However problematic this is for residential bedrooms, it is an even more serious problem for hotels and the like. With respect to such commercial bedrooms there is more opportunity for external infection sources to bring bed bugs to the site, and should there be an unknown infestation which causes biting of customers before it is dealt with, there is a severe risk of customer dissatisfaction and adverse publicity, likely leading to a long term significant reputation loss.

There have been attempts to control bed bug infestation through applications of insecticidal chemicals to infected areas and materials (especially mattresses). This approach has some drawbacks. For example, it can expose those using a treated area or mattress too soon after application to odor or other undesired characteristics of the pesticidal chemical. Further, unless the chemicals are used regularly, without regard to whether an infestation is known to already exist (a procedure which will significantly increase costs), those sleeping in an infected area can be bitten before one knows to begin treatment.

Another reason for the increase in bed bugs is that pest control services more often nowadays use low toxicity gel-based pesticides for control of cockroaches, the most common pest in structures, instead of residual sprays. When residual sprays meant to kill other insects were commonly being used, they resulted in a collateral insecticidal effect on potential bed bug infestations; the gel-based insecticides primarily used nowadays do not have any effect on bed bugs, as they are incapable of feeding on these baits.

There is, therefore, a need for safe and effective chemicals to control or repel bed bugs and for safe and effective means to employ such chemicals for the control or repellency of bed bugs.

SUMMARY OF THE INVENTION

In accordance with this invention, control and repellency of bed bugs is obtained by contact of the bed bugs with an inhibitory effective amount of at least one of the compounds of the structure (I)

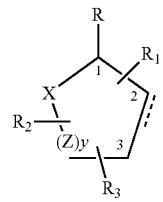

wherein
R is selected from —OH, —OC(O)$R_4$, —O$R_6$, —(O$R_6$)$_2$, wherein each $R_6$ is independently selected from an alkyl group containing from 1 to 4 carbon atoms and $R_4$ is a branched or straight chain, saturated or unsaturated hydrocarbyl group with zero to two double bonds and from 1 to 15 carbon atoms;
X is O or $CH_2$, with the proviso that when X is O R can only be =O;
each Z is independently selected from (CH) and ($CH_2$);
y is a numeral selected from 1 and 2;
$R_1$ is selected from H or a branched or straight chain, saturated or unsaturated hydrocarbyl group with zero to two double bonds and from 1 to 15 carbon atoms;
$R_2$ is selected from H and a branched or straight chain, saturated or unsaturated hydrocarbyl group with zero to three double bonds and from 1 to 15 carbon atoms;
$R_3$ is selected from H, a branched or straight chain, saturated or unsaturated hydrocarbyl group with zero to three double bonds and from 1 to 15 carbon atoms, $(CH_2)_n$OH, —C(O)O$R_5$, —$CH_2$C(O)O$R_7$, —$CH_2$C(O)$R_8$, —C(O)N$R_9R_{10}$, —$CH_2$C(O)N$R_{11}R_{12}$ where each of $R_5$, $R_7$, $R_8$, $R_9$, $R_{10}$, $R_{11}$ and $R_{12}$ is independently selected from H and a branched or straight chain, saturated or unsaturated hydrocarbyl group with zero to three double bonds and from 1 to 15 carbon atoms and n is an integer of from 1 to 12; and
the bond between the 2 and 3 positions in the ring structure may be a single or a double bond, and wherein the compounds of structure (1) contain from 11 to 20 total carbon atoms, except where R is =O, X=$CH_2$ and y is 1 the compounds of structure (I) contain from 13 to 20 total carbon atoms in the compounds. The invention also includes optical isomers, diastereomers and enantiomers of the named structures. Thus, at all stereocenters where stereochemistry is not explicitly defined, all possible epimers are envisioned.

Safe and effective control or repellency of bed bugs can be accomplished with the use of formulations containing at least one compound selected from Structure I as described above. The compounds may be present in any of their isomeric or enantiomeric forms or as mixtures of their isomers or enantiomers. Additionally, they may be used in conjunction with established pesticides or toxicants, including but not limited to N,N-Diethyl-m-toluamide (DEET®) and para-methane-3,8-diol (PMD).

Further aspects of this invention relate to the use of such formulations in various methods for the control or repellency of bed bugs. Among the various methods in which the formulations of this invention may be employed are (1) injecting the formulations into a mattress, either directly or in combination with other ingredients or solvents, (2) placing the formulations on an absorbent material and placing the absorbent material in a sachet and placing the sachet containing the formulation into a locus such as, including but not limited to, a mattress, hamper, suitcase, clothing bag, linen storage closet or any other enclosure where bed bugs may be present, (3) preparing "dryer sheets" containing the formulations for placement in a locus such as, including but not limited to, a mattress, suitcase, clothing bag, hamper, clothing bag, linen storage closet, or any other enclosure where bed bugs are likely to be present, or in a pile of clean or soiled laundry, (4) placing the formulation into detergent or fabric softener compositions for controlling bed bugs during use of these compositions in cleaning clothes and sprays or in carpet or floor cleaner products and the like to treat carpets and furniture, (5) spraying a formulation containing the compounds of structure (I) with or without a co-formulant such as DEET® or PMD on surfaces, fabric, or luggage and (6) topical application of the formulation intended for use with humans or animals, such as in the form of, including but not limited to, a lotion, wipes, powder, spray or shampoo.

DETAILED DESCRIPTION OF THE INVENTION

Control and repellency of bed bugs is obtained by contact of the bed bugs with an inhibitory effective amount of at least one of the compounds of the structure (I)

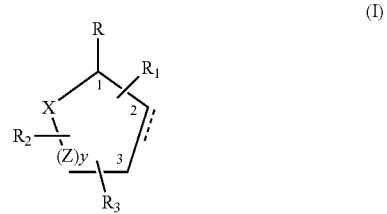

(I)

wherein
R is selected from —OH, —OC(O)$R_4$, —OR$_6$, —(OR$_6$)$_2$, wherein each $R_6$ is independently selected from an alkyl group containing from 1 to 4 carbon atoms and $R_4$ is a branched or straight chain, saturated or unsaturated hydrocarbyl group with zero to two double bonds and from 1 to 15 carbon atoms;
X is O or $CH_2$, with the proviso that when X is O R can only be =O;
each Z is independently selected from (CH) and ($CH_2$);
y is a numeral selected from 1 and 2;
$R_1$ is selected from H or a branched or straight chain, saturated or unsaturated hydrocarbyl group with zero to two double bonds and from 1 to 15 carbon atoms;
$R_2$ is selected from H and a branched or straight chain, saturated or unsaturated hydrocarbyl group with zero to three double bonds and from 1 to 15 carbon atoms;
$R_3$ is selected from H, a branched or straight chain, saturated or unsaturated hydrocarbyl group with zero to three double bonds and from 1 to 15 carbon atoms, —($CH_2$)$_n$OH, —C(O)OR$_5$, —$CH_2$C(O)OR$_7$, —$CH_2$C(O)R$_8$, —C(O)NR$_9$R$_{10}$, —$CH_2$C(O)NR$_{11}$R$_{12}$ where each of $R_5$, $R_7$, $R_8$, $R_9$, $R_{10}$, $R_{11}$ and $R_{12}$ is independently selected from H and a branched or straight chain, saturated or unsaturated hydrocarbyl group with zero to three double bonds and from 1 to 15 carbon atoms, and n is an integer of from 1 to 12; and
the bond between the 2 and 3 positions in the ring structure may be a single or a double bond, and wherein the compounds of structure (1) contain from 11 to 20 total carbon atoms, except where R is =O, X=$CH_2$ and y is 1 the compounds of structure (I) contain from 13 to 20 total carbon atoms in the compounds. The invention also includes optical isomers, diastereomers and enantiomers of the named structures. Thus, at all stereocenters where stereochemistry is not explicitly defined, all possible epimers are envisioned.

A preferred group of control and repellency compounds are those compounds of Structure (I) wherein
R is selected from —OH, X is $CH_2$, y is 1 or 2, each Z is selected from (CH) and ($CH_2$), the bond between positions 2 and 3 in the ring is a single bond, one of $R_1$ and $R_2$ is H or —$CH_3$ and the other of $R_1$ and $R_2$ is a branched or unbranched, saturated or unsaturated hydrocarbyl group containing group containing from 9 to 15 carbon atoms and 0 to 3 double bonds, and $R_3$ is H.

Another preferred group of control and repellency compounds are those compounds of structure (I) wherein
R is selected from —OH, X is $CH_2$, y is 1 or 2, more preferably 1, each Z is selected from (CH) and ($CH_2$), the bond between positions 2 and 3 in the ring is a single or double bond, more preferably a single bond, one of $R_1$ and $R_2$ is H and the other of $R_1$ and $R_2$ is a branched or unbranched, saturated or unsaturated hydrocarbyl group containing from 9 to 15 carbon atoms and 0 to 3 double bonds, and $R_3$ is selected from —C(O)OR$_5$ and —$CH_2$C(O)R$_8$ where $R_5$ and $R_8$ are each selected from a branched or unbranched, saturated or unsaturated hydrocarbyl group containing from 1 to 6 carbon atoms, and more preferably 3 to 5 carbon atoms and still more preferably are —$CH_3$.

Representative examples of compounds of structure (I) include, but are not limited to,

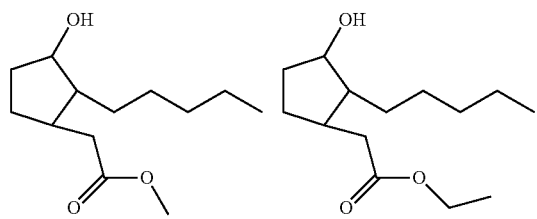

methyl 2-(3-hydroxy-2-pentyl-cyclopentyl)acetate
Chemical Formula: $C_{13}H_{24}O_3$
Molecular Weight: 228.33
Methyl Dihydro Jasmolate ethyl 2-(3-hydroxy-2-pentyl-cyclopentyl)acetate
Chemical Formula: $C_{14}H_{26}O_3$
Molecular Weight: 242.35
Ethyl Dihydro Jasmolate

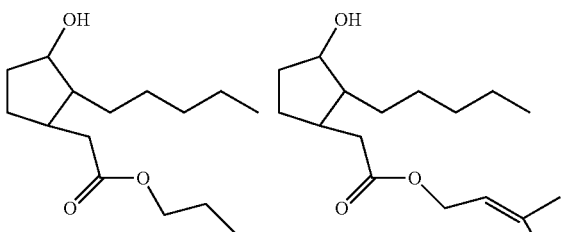

propyl 2-(3-hydroxy-2-pentyl-cyclopentyl)acetate
Chemical Formula: $C_{15}H_{28}O_3$
Molecular Weight: 256.38
Propyl Dihydro Jasmolate 3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate -continued

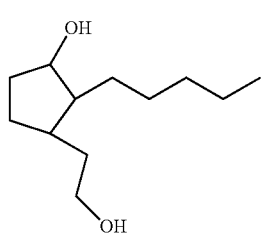

3-(2-hydroxyethyl)-2-
pentylcyclopentanol
Chemical Formula: $C_{12}H_{24}O_2$
Molecular Weight: 200.32
MethylDihydroJasmodiol

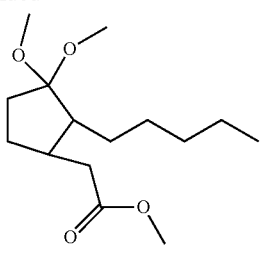

methyl 2-(3,3-dimethoxy-2-
pentylcyclopentyl)acetate
Chemical Formula: $C_{15}H_{28}O_4$
Molecular Weight: 272.38
Methyl Dihydro Jasmonate
Dimethyl Ketal

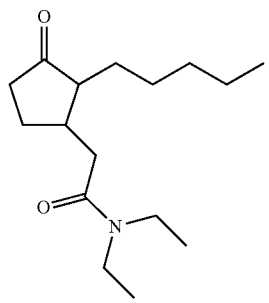

N,N-diethyl-2-(3-oxo-2-pentyl-
cyclopentyl)acetamide
Chemical Formula: $C_{16}H_{29}NO_2$
Molecular Weight: 267.41
MDJ Amide

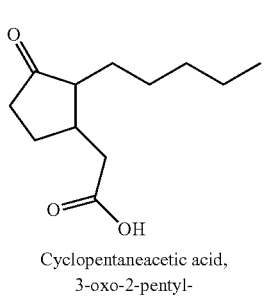

Cyclopentaneacetic acid,
3-oxo-2-pentyl-
Chemical Formula: $C_{12}H_{20}O_3$
Molecular Weight: 212.29
CAS 3572-64-3
Dihydrojasmonic acid

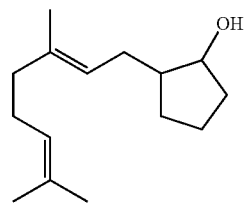

(E)-2-(3,7-dimethylocta-2,6-
dienyl)cyclopentanol
Chemical Formula: $C_{15}H_{26}O$
Molecular Weight: 222.37
Apritol

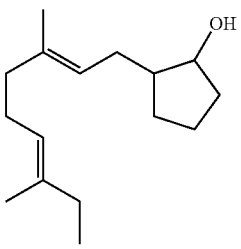

2-((2E,6E)-3,7-dimethylnona-
2,6-dienyl)cyclopentanol
Chemical Formula: $C_{16}H_{28}O$
Molecular Weight: 236.39
Methyl Apritol

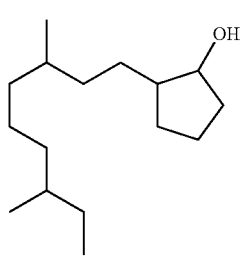

2-(3,7-dimethylnonyl)-
cyclopentanol
Chemical Formula: $C_{16}H_{32}O$
Molecular Weight: 240.42
Tetrahydromethyl Apritol -continued

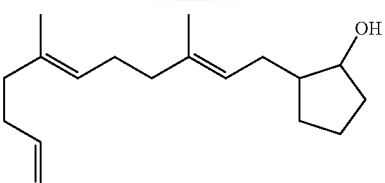

2-((2E,6E)-3,7,11-trimethyldodeca-
2,6,10-trienyl)cyclopentanol
Chemical Formula: $C_{20}H_{34}O$
Molecular Weight: 290.48
Farnesylcyclopentanol

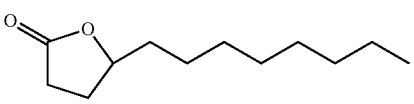

5-octyldihydrofuran-2(3H)-one
Chemical Formula: $C_{12}H_{22}O_2$
Molecular Weight: 198.30
gamma-dodecalactone

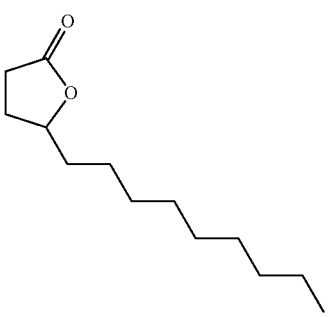

5-nonyldihydrofuran-2(3H)-one
Chemical Formula: $C_{13}H_{24}O_2$
Molecular Weight: 212.33
Gamma-Tridecalactone

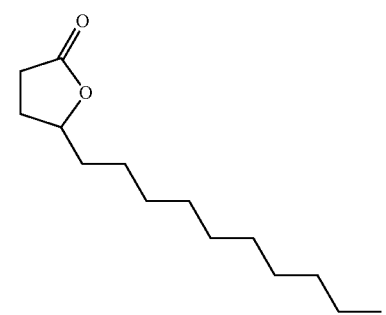

5-decyldihydrofuran-2(3H)-one
Chemical Formula: $C_{14}H_{26}O_2$
Molecular Weight: 226.36
Gamma-Tetradecalactone

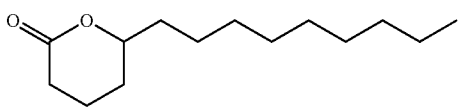

6-nonyltetrahydro-2H-pyran-2-one
Chemical Formula: $C_{14}H_{26}O_2$
Molecular Weight: 226.36
Delta-Tetradecalactone -continued

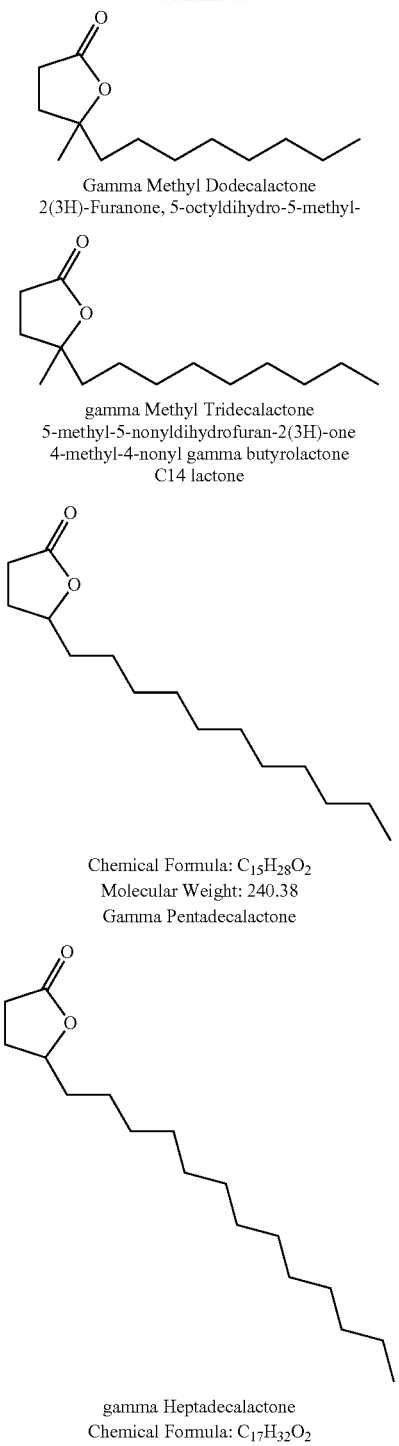

Gamma Methyl Dodecalactone
2(3H)-Furanone, 5-octyldihydro-5-methylgamma Methyl Tridecalactone
5-methyl-5-nonyldihydrofuran-2(3H)-one
4-methyl-4-nonyl gamma butyrolactone
C14 lactone Chemical Formula: $C_{15}H_{28}O_2$
Molecular Weight: 240.38
Gamma Pentadecalactone gamma Heptadecalactone
Chemical Formula: $C_{17}H_{32}O_2$
Molecular Weight: 268.24

Chemical Formula: $C_{11}H_{20}O$
Molecular Weight: 168.28
3-methyl-5-isobutyl-2-cyclohexen-1-ol -continued

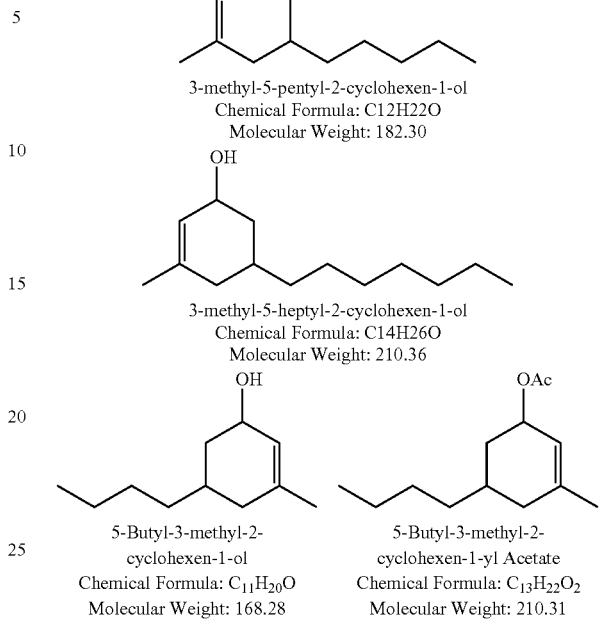

3-methyl-5-pentyl-2-cyclohexen-1-ol
Chemical Formula: $C_{12}H_{22}O$
Molecular Weight: 182.30

3-methyl-5-heptyl-2-cyclohexen-1-ol
Chemical Formula: $C_{14}H_{26}O$
Molecular Weight: 210.36

5-Butyl-3-methyl-2-cyclohexen-1-ol
Chemical Formula: $C_{11}H_{20}O$
Molecular Weight: 168.28

5-Butyl-3-methyl-2-cyclohexen-1-yl Acetate
Chemical Formula: $C_{13}H_{22}O_2$
Molecular Weight: 210.31

A group of especially preferred compounds of structure (I) is gamma-dodecalactone, gamma-tridecalactone, gamma-pentadecalactone, methyl apritol, methyl dihydrojasmolate, methyl dihydrojasmolate dimethyl acetal, and 3-methyl-5-pentyl-2-cyclohexenone.

The inhibitory effective amount of the compounds of structure (I) to control or repel the bed bugs will be dependent upon the compound employed and the manner in which it is employed and will be readily determined by the user. In general the inhibitory effective amount will be in an amount of from about 0.1% to about 10% by weight, more preferably from about 0.1% to about 5% by weight, and more preferably from about 0.1% to about 2% by weight, in a carrier.

The invention is illustrated by, but not limited to, the following examples.

Two semicircle discs of paper, one treated (1 ml of acetone solution of each compound was applied to each disc) and one untreated (1 ml of acetone only), were placed in the lid of a Petri dish. Control arenas were set up in a similar fashion with two untreated discs of paper. Five replicates of 10 bed bugs were released into the centers of the lids and were thus presented with a choice of treated vs. untreated substrate (or untreated vs. untreated in the control arenas). The distribution of the bed bugs was recorded at 2 hours post-treatment. Paired t-tests were conducted for each treatment to ascertain whether or not there was a statistically significant difference in the numbers of bed bugs on the treated vs. untreated discs. Repellency, as avoidance, is given in the table below.

TABLE 1

| Compound | Repellency/Avoidance |
| --- | --- |
| DEET (0.09%) | 66% |
| DEET (0.2%) | 74% |

TABLE 1-continued

| Compound | Repellency/Avoidance |
|---|---|
| Para Menthane-3,8-diol (PMD) (0.15%) | 42% |
| Para Menthane-3,8-diol (PMD) (0.2%) | 70% |
| Methyl dihydrojasmolate (0.15%) | 58% |
| Methyl dihydrojasmolate (0.2%) | 82% |
| Methyl dihydrojasmonate dimethyl acetal (0.2%) | 90% |
| Methyl dihydrojasmonate amide | 28% |
| Prenyl dihydrojasmolate (0.2%) | 48% |
| Dihydrojasmolactone (0.2%) | 84% |
| Dihydrojasmonic Acid (0.2%) | 78% |
| gamma-Dodecalactone (0.2%) | 82% |
| gamma-Tridecalactone (0.5%) | 86% |
| gamma-Tridecalactone (1%) | 96% |
| gamma-Pentadecalactone (1%) | 92% |
| gamma-Heptadecalactone (2%) | 68% |
| gamma Methyl tridecalactone (0.2%) | 72% |
| 50:50 PMD and gamma Methyl tridecalactone (0.2%) | 98% |
| Methyl apritol (0.15%) | 74% |
| Methyl apritol (0.2%) | 88% |

While the invention has been described herein with reference to the specific embodiments thereof, it will be appreciated that changes, modifications and variations can be made without departing from the scope of the inventive concept disclosed herein, and it is intended to embrace all such changes, modification and variations that fall with the scope of the appended claims.

I claim:

1. A method for the control or repellency of bed bugs, the method comprising contacting the bed bugs with an inhibitory effective amount of an inhibitory compound, wherein the inhibitory compound consists essentially of:

(i) at least one of the compounds of the structure (I)

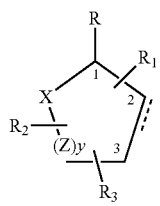

wherein
R is =O;
X is O;
each Z is independently selected from the group consisting of (CH) and (CH$_2$);
y is a numeral selected from 1 and 2;
R$_1$ is selected from the group consisting of H and a branched or straight chain, saturated or unsaturated hydrocarbyl group with zero to two double bonds and from 1 to 15 carbon atoms;
R$_2$ is selected from the group consisting of H and a branched or straight chain, saturated or unsaturated hydrocarbyl group with zero to three double bonds and from 1 to 15 carbon atoms;
R$_3$ is selected from H, a branched or straight chain, saturated or unsaturated hydrocarbyl group with zero to three double bonds and from 1 to 15 carbon atoms, —(CH$_2$)$_n$OH, —C(O)OR$_5$, —CH$_2$C(O)OR$_7$, —C(O)NR$_9$R$_{10}$, —CH$_2$C(O)NR$_{11}$R$_{12}$ where each of R$_5$, R$_7$, R$_9$, R$_{10}$, R$_{11}$ and R$_{12}$ is independently selected from the group consisting of H and a branched or straight chain, saturated or unsaturated hydrocarbyl group with zero to three double bonds and from 1 to 15 carbon atoms, and n is an integer of from 1 to 12;

the bond between the 2 and 3 positions in the ring structure may be a single or a double bond, wherein the compounds of structure (1) contain from 11 to 20 total carbon atoms;

(ii) at least one compound of structure (I) in combination with N,N-Diethyl-m-toluamide (DEET®);

(iii) at least one compound of structure (I) in combination with para-Menthane-3,8-diol (PMD); or (iv) at least one compound of structure (I) in combination with any other compound of structure (I).

2. The method according to claim 1 wherein the compounds of structure (1) have from 12 to 16 carbon atoms in the compound.

3. The method according to claim 1 wherein the at least one compound of structure (I) is selected from the group consisting of:

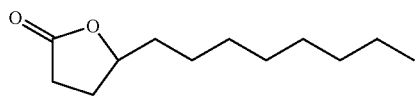

5-octyldihydrofuran-2(3H)-one
Chemical Formula: C$_{12}$H$_{22}$O$_2$
Molecular Weight: 198.30
gamma-dodecalactone

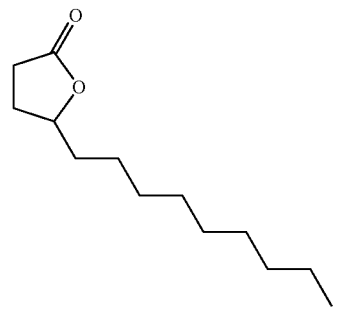

5-nonyldihydrofuran-2(3H)-one
Chemical Formula: C$_{13}$H$_{24}$O$_2$
Molecular Weight: 212.33
Gamma-Tridecalactone

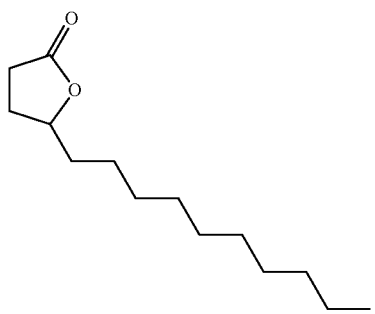

5-decyldihydrofuran-2(3H)-one
Chemical Formula: C$_{14}$H$_{26}$O$_2$
Molecular Weight: 226.36
Gamma-Tetradecalactone -continued

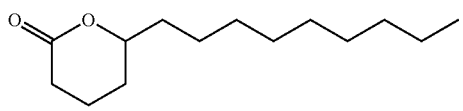

6-nonyltetrahydro-2H-pyran-2-one
Chemical Formula: $C_{14}H_{26}O_2$
Molecular Weight: 226.36
Delta-Tetradecalactone

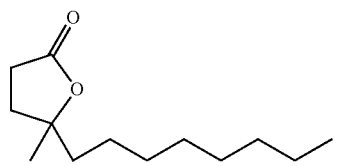

Gamma Methyl Dodecalactone
2(3H)-Furanone, 5-octyldihydro-5-methyl-

5-methyl-5-nonyldihydrofuran-2(3H)-one
4-methyl-4-nonyl gamma butyrolactone
C14 lactone

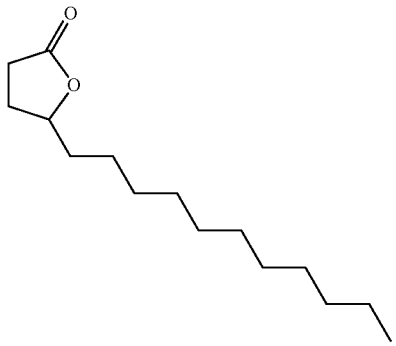

Chemical Formula: $C_{15}H_{28}O_2$
Molecular Weight: 240.38
Gamma Pentadecalactone

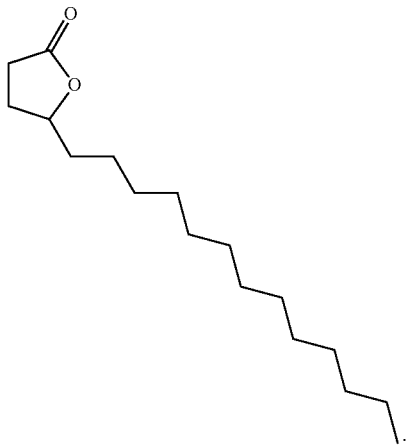

gamma Heptadecalactone
Chemical Formula: $C_{17}H_{32}O_2$
Molecular Weight: 268.24 and

4. The method according to claim 1 wherein the beg bugs are contacted with at least one compound of structure (I) in combination with N,N-Diethyl-m-toluamide (DEET®).

5. The method according to claim 1 wherein the bed bugs are contacted with at least one compound of structure (I) in combination with para-Menthane-3,8-diol (PMD).

6. The method according to claim 1 wherein the bed bugs are contacted with at least one compound of structure (I) in combination with any other compound of structure (I).

7. The method according to claim 1 wherein the at least one compound of structure (I) is applied to surface of or impregnated into clothing or fabric.

8. The method according to claim 1 wherein the at least one compound of structure (I) is applied to detergents, fabric softeners or dryer sheets.

9. The method according to claim 1 wherein the at least one compound of structure (I) is applied as a topical repellent in lotion, wipes, powder, spray or shampoo.

10. The method according to claim 1 wherein the at least one compound of structure (I) is selected from the group consisting of gamma-dodecalactone, gamma-tridecalactone, and gamma-pentadecalactone.

11. The method according to claim 1 wherein the inhibitory effective amount is from about 0.1% to about 10% by weight in a carrier.

12. A method for the control or repellency of bed bugs, the method comprising contacting the bed bugs with an inhibitory effective amount of at least one inhibitory compound, wherein the inhibitory compound consists essentially of a compound selected from the group consisting of:

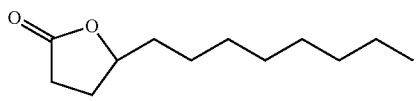

5-octyldihydrofuran-2(3H)-one
Chemical Formula: $C_{12}H_{22}O_2$
Molecular Weight: 198.30
gamma-dodecalactone

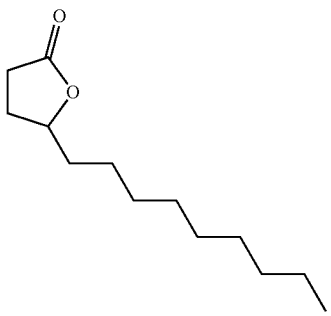

5-nonyldihydrofuran-2(3H)-one
Chemical Formula: $C_{13}H_{24}O_2$
Molecular Weight: 212.33
Gamma-Tridecalactone -continued

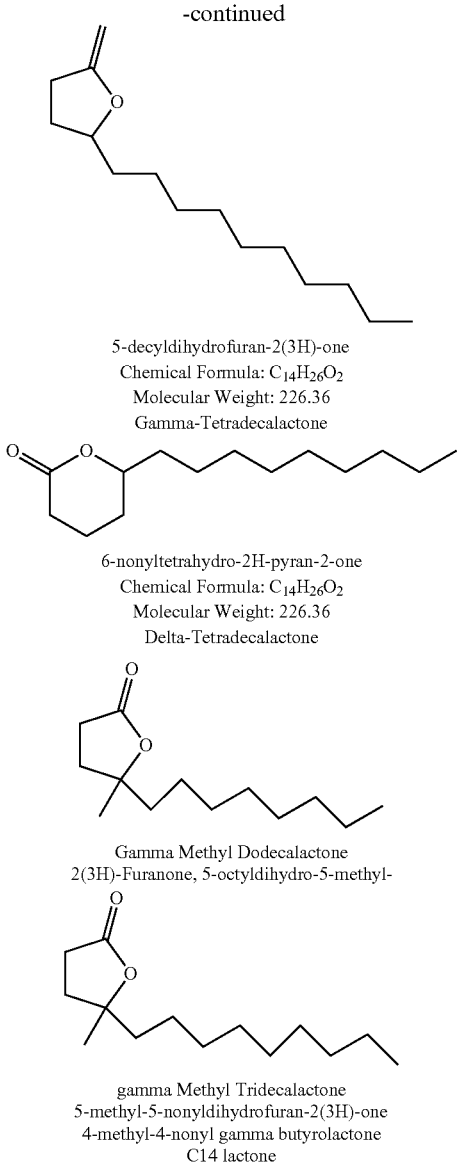

5-decyldihydrofuran-2(3H)-one
Chemical Formula: $C_{14}H_{26}O_2$
Molecular Weight: 226.36
Gamma-Tetradecalactone 6-nonyltetrahydro-2H-pyran-2-one
Chemical Formula: $C_{14}H_{26}O_2$
Molecular Weight: 226.36
Delta-Tetradecalactone Gamma Methyl Dodecalactone
2(3H)-Furanone, 5-octyldihydro-5-methylgamma Methyl Tridecalactone
5-methyl-5-nonyldihydrofuran-2(3H)-one
4-methyl-4-nonyl gamma butyrolactone
C14 lactone -continued

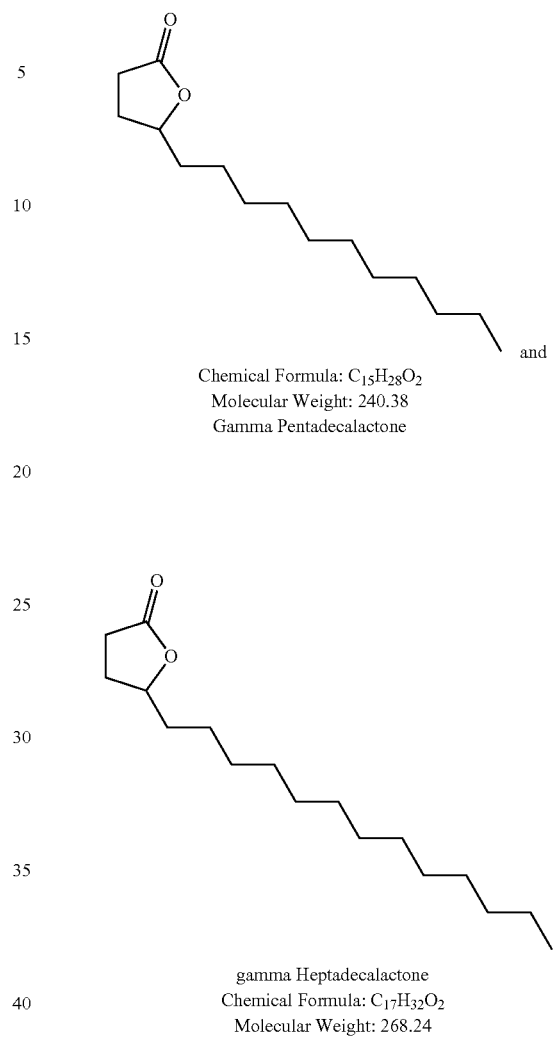

Chemical Formula: $C_{15}H_{28}O_2$
Molecular Weight: 240.38
Gamma Pentadecalactone and gamma Heptadecalactone
Chemical Formula: $C_{17}H_{32}O_2$
Molecular Weight: 268.24

* * * * *